(12) United States Patent
Woods et al.

(10) Patent No.: US 11,976,848 B2
(45) Date of Patent: May 7, 2024

(54) SYSTEMS AND METHODS FOR TREATMENT OF AIR

(71) Applicant: SPECTRALANCE, LLC, Beverly Hills, CA (US)

(72) Inventors: Carla Mann Woods, Beverly Hills, CA (US); Timothy Nugent, Playa Del Rey, CA (US); Mark Westcott, Battle Ground, WA (US); Arsen Norman Tokhmakhian, Van Nuys, CA (US)

(73) Assignee: Spectralance, LLC, Beverly Hills, CA (US)

( * ) Notice: Subject to any disclaimer, the term of this patent is extended or adjusted under 35 U.S.C. 154(b) by 0 days.

(21) Appl. No.: 18/344,636

(22) Filed: Jun. 29, 2023

(65) Prior Publication Data

US 2023/0341139 A1  Oct. 26, 2023

Related U.S. Application Data

(63) Continuation of application No. PCT/US2021/065839, filed on Dec. 31, 2021.
(Continued)

(51) Int. Cl.
*F24F 8/80* (2021.01)
*A61L 9/20* (2006.01)
(Continued)

(52) U.S. Cl.
CPC .............. *F24F 8/80* (2021.01); *A61L 9/20* (2013.01); *B01D 46/0005* (2013.01);
(Continued)

(58) Field of Classification Search
CPC . B01D 46/0005; B01D 46/0027; B01D 50/00
See application file for complete search history.

(56) References Cited

U.S. PATENT DOCUMENTS 6,949,223 B2 * 9/2005 McEllen .................. A61L 9/20
250/435
7,771,672 B2  8/2010 Bergeron et al.
(Continued)

FOREIGN PATENT DOCUMENTS

CA  3124554 A1  2/2022
CN  204113696 U  *  1/2015
(Continued)

OTHER PUBLICATIONS

Search Report and Written Opinion issued in International Application No. PCT/US2021/065839, dated Jun. 27, 2022 (24 pages).
(Continued)

*Primary Examiner* — Robert A Hopkins
(74) *Attorney, Agent, or Firm* — BLAIR WALKER IP SERVICES, LLC

(57) ABSTRACT

An air purifying system for an indoor space includes a plurality of air purifying sites, each one of the plurality of air purifying sites configured to treat a sub-volume of the total volume of air in the indoor space, wherein each one of the plurality of air purifying sites includes a housing, an air inlet configured to direct treatment air having gaseous and non-gaseous components from the indoor space into the housing, a purifier carried within the housing, an air outlet configured to direct the treatment air that has passed through the purifier into the indoor space, and an air mover configured to move air between the air inlet and the air outlet, through the purifier, wherein the plurality of air purifying sites is configured to work cooperatively with a central air system of the indoor space.

28 Claims, 12 Drawing Sheets

Related U.S. Application Data

(60) Provisional application No. 63/133,198, filed on Dec. 31, 2020.

(51) Int. Cl.
  B01D 46/00 (2022.01)
  B01D 50/00 (2022.01)
  F24F 8/108 (2021.01)
  F24F 8/22 (2021.01)

(52) U.S. Cl.
  CPC ......... B01D 46/0027 (2013.01); B01D 50/00 (2013.01); F24F 8/108 (2021.01); F24F 8/22 (2021.01); *A61L 2209/111* (2013.01); *A61L 2209/14* (2013.01)

(56) References Cited

U.S. PATENT DOCUMENTS

| | | | |
|---|---|---|---|
| 8,252,099 | B2 | 8/2012 | Worrilow |
| 10,933,158 | B2* | 3/2021 | Benedek ............... B01J 35/004 |
| 2002/0094298 | A1 | 7/2002 | Monagan |
| 2004/0258581 | A1 | 12/2004 | Wei et al. |
| 2005/0129589 | A1 | 6/2005 | Wei et al. |
| 2005/0129591 | A1 | 6/2005 | Wei et al. |
| 2007/0102280 | A1 | 5/2007 | Hunter et al. |
| 2007/0207066 | A1 | 9/2007 | Thur et al. |
| 2007/0266855 | A1 | 11/2007 | Fleisher |
| 2008/0093210 | A1 | 4/2008 | Edwards |
| 2008/0141864 | A1 | 6/2008 | McCarthy |
| 2008/0260601 | A1 | 10/2008 | Lyon |
| 2009/0004047 | A1 | 1/2009 | Hunter et al. |
| 2009/0041632 | A1 | 2/2009 | Day et al. |
| 2011/0171080 | A1 | 7/2011 | Lo |
| 2011/0171090 | A1 | 7/2011 | Johnson et al. |
| 2013/0052090 | A1 | 2/2013 | Bohlen |
| 2015/0078960 | A1 | 3/2015 | Krosney et al. |
| 2017/0246333 | A1 | 8/2017 | Cabone et al. |
| 2017/0356672 | A1* | 12/2017 | Kim .................. F24F 11/30 |
| 2018/0264157 | A1 | 9/2018 | Benedek et al. |
| 2018/0264160 | A1 | 9/2018 | Benedek et al. |
| 2019/0063763 | A1 | 2/2019 | Kleinberger et al. |
| 2019/0240370 | A1 | 8/2019 | Benedek et al. |
| 2019/0240371 | A1 | 8/2019 | Benedek et al. |
| 2021/0283544 | A1 | 9/2021 | Jennings et al. |
| 2021/0290793 | A1 | 9/2021 | Tung |
| 2021/0350312 | A1 | 11/2021 | Swift et al. |
| 2021/0372561 | A1 | 12/2021 | Swift et al. |
| 2022/0008597 | A1 | 1/2022 | Bergman |
| 2023/0115249 | A1 | 4/2023 | Wang |

FOREIGN PATENT DOCUMENTS

| | | | |
|---|---|---|---|
| CN | 206131194 U | | 4/2017 |
| CN | 110375399 A | | 10/2019 |
| CN | 111637565 A | | 9/2020 |
| EP | 3920317 A1 | | 12/2021 |
| JP | 2003-112014 A | | 4/2003 |
| JP | 2016142489 A | * | 8/2016 |
| TW | M572475 U | | 1/2019 |
| WO | WO2018/149980 A1 | | 8/2018 |
| WO | WO2021/216611 A1 | | 10/2021 |
| WO | WO2021/235951 A1 | | 11/2021 |

OTHER PUBLICATIONS

"Ex-Gov. Rick Perry is part of company marketing 'catch and kill' device to battle COVID" John C. Moritz, Austin American Statesman, Aug. 24, 2021 (6 pages).

* cited by examiner

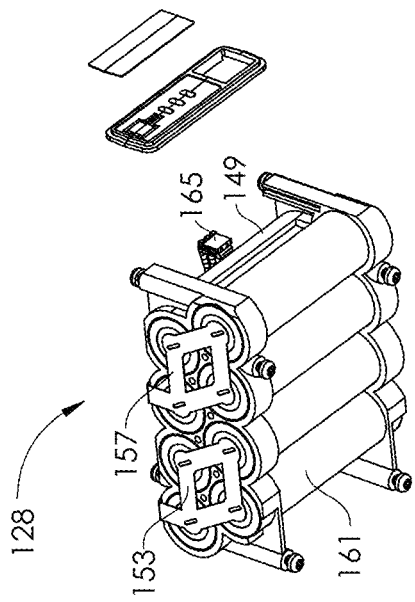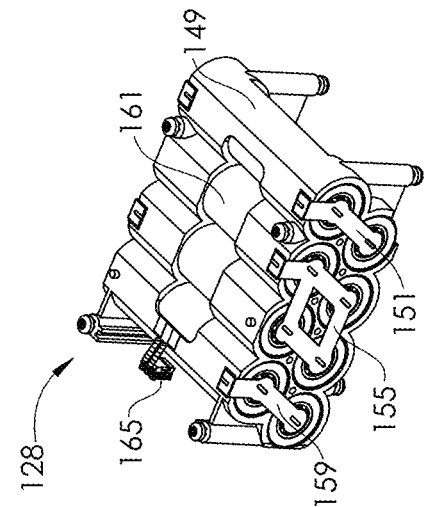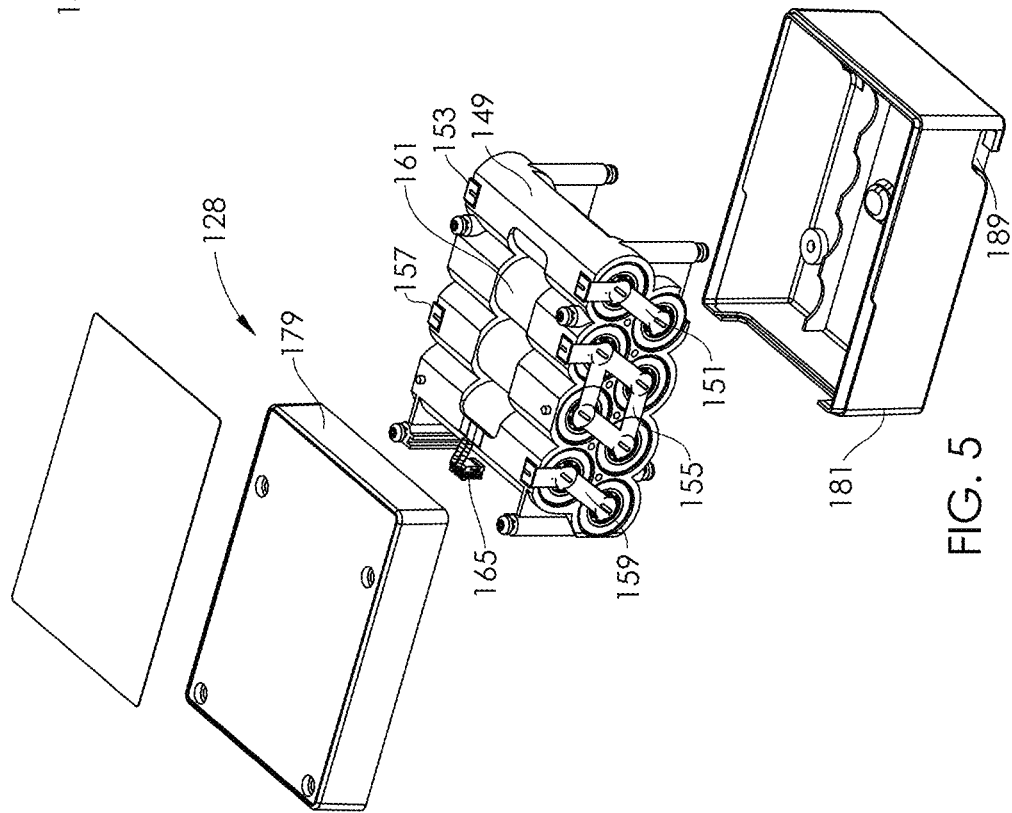

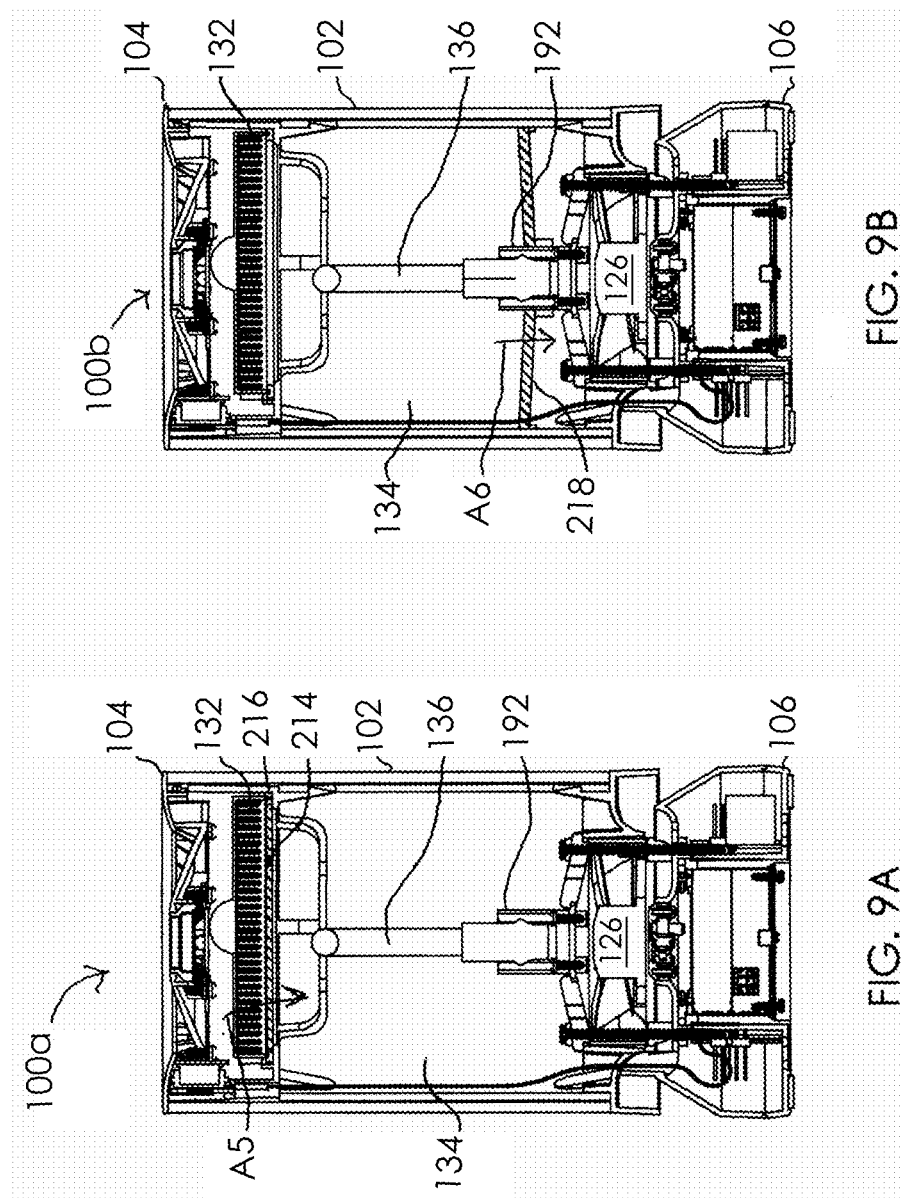

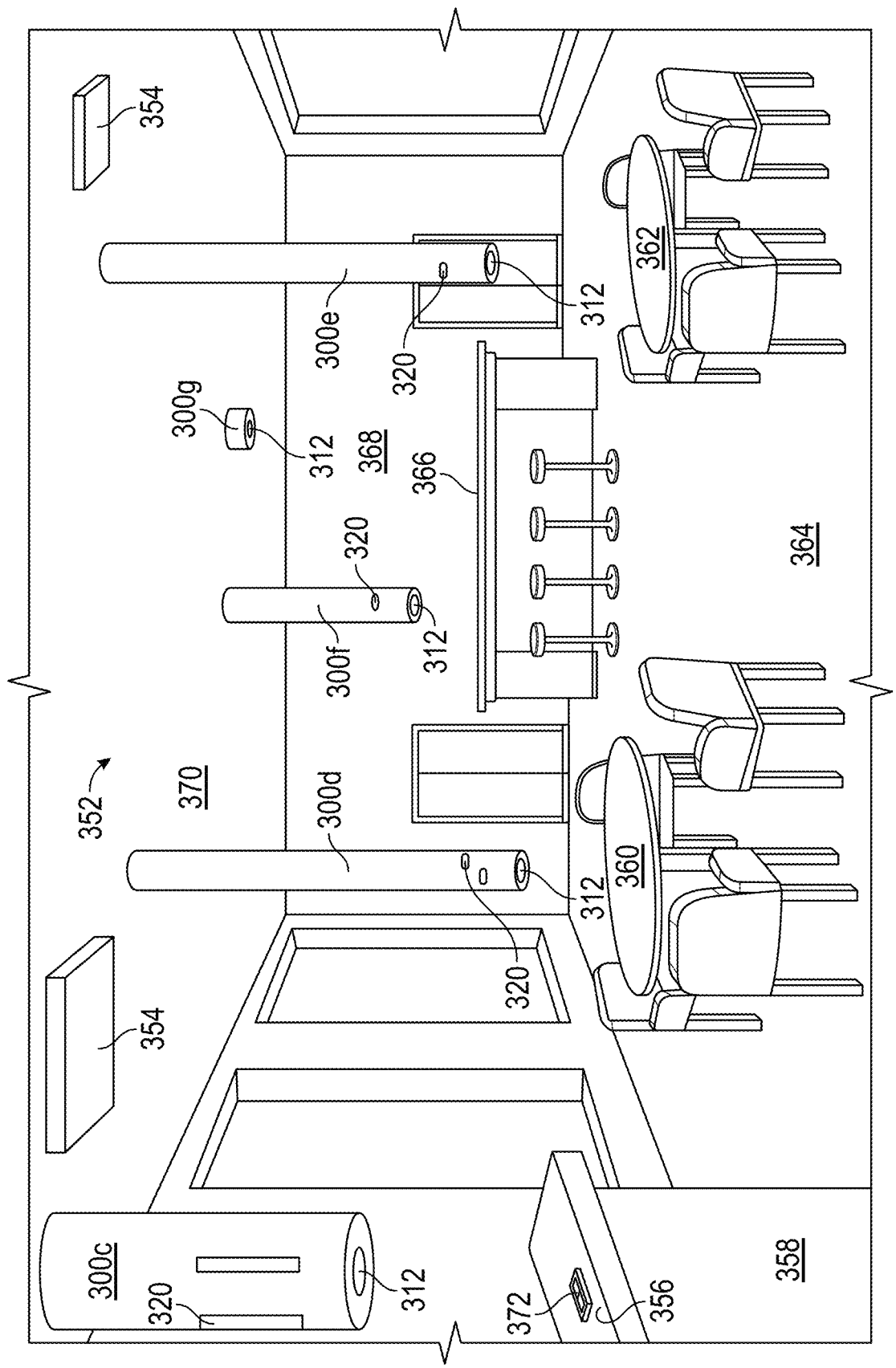

SYSTEMS AND METHODS FOR TREATMENT OF AIR

INCORPORATION BY REFERENCE TO ANY PRIORITY APPLICATIONS

This application is a continuation of international application no. PCT/US2021/065839, filed on Dec. 31, 2021, which claims the benefit of priority to U.S. Provisional Application No. 63/133,198, filed on Dec. 31, 2020, both of which are incorporated by reference in their entirety herein for all purposes. Priority is claimed pursuant to 35 U.S.C. § 120 and 35 U.S.C. § 119.

BACKGROUND OF THE INVENTION

Field of the Invention

The disclosed and described technology relates generally to treatment, e.g. purification, of air supplied to human living or working spaces. For example, by separation, e.g. by filtering, and/or by sterilizing using UV light. The air purifiers may be self-contained and/or may be part of a heating, ventilation, and air conditioning (HVAC) system.

SUMMARY OF THE INVENTION

In a first embodiment of the present disclosure, an air purifying system for an indoor space includes a plurality of air purifiers, each one of the plurality of air purifiers configured to filter a sub-volume of the total volume of air in the indoor space, each one of the plurality or air purifiers fully powered by a rechargeable power supply and not requiring wired connection to wall power, each one of the plurality of air purifiers configured to sit on a floor or table top and having an effective footprint of no more than one foot, wherein each one of the plurality of air purifiers includes a housing, an air inlet configured to direct treatment air having gaseous and non-gaseous components from the indoor space into the housing, a first filter configured to filter the treatment air from the air inlet, a UV lamp carried within a UV treatment space in the housing and configured to deliver UV light to the treatment air that has passed through the first filter, an air outlet configured to direct the treatment air that has passed through the UV treatment space into the indoor space, and an air mover configured to move air between the air inlet and the air outlet, through the first filter and the UV treatment space, wherein the plurality of air purifiers is configured to work cooperatively with a central air system of the indoor space.

In another embodiment of the present disclosure, an air purifying system for an indoor space includes a plurality of air purifiers, each one of the plurality of air purifiers configured to filter a sub-volume of the total volume of air in the indoor space, each one of the plurality or air purifiers fully powered by a rechargeable power supply and not requiring wired connection to wall power, each one of the plurality of air purifiers configured to sit on a table top and having an effective footprint that does not impede the use of the table by at least two users, wherein each one of the plurality of air purifiers includes a housing, an air inlet configured to direct treatment air having gaseous and non-gaseous components from the indoor space into the housing, a first filter configured to filter the treatment air from the air inlet, a UV lamp carried within a UV treatment space in the housing and configured to deliver UV light to a first portion of the treatment air that has passed through the first filter; an air outlet configured to direct a second portion of the treatment air that has passed through UV treatment space into the indoor space, and an air mover configured to move air between the air inlet and the air outlet, through the first filter and the UV treatment space.

In still another embodiment of the present disclosure, an air purifying system for an indoor space includes a plurality of air purifying sites, each one of the plurality of air purifying sites configured to treat a sub-volume of the total volume of air in the indoor space, wherein each one of the plurality of air purifying sites includes a housing, an air inlet configured to direct treatment air having gaseous and non-gaseous components from the indoor space into the housing, a purifier carried within the housing, an air outlet configured to direct the treatment air that has passed through the purifier into the indoor space, and an air mover configured to move air between the air inlet and the air outlet, through the purifier, wherein the plurality of air purifying sites is configured to work cooperatively with a central air system of the indoor space.

In yet another embodiment of the present disclosure, a wireless air purifier includes a housing having a top and a bottom, an air inlet at or adjacent the top of the housing, a first filter within the housing configured to directly receive air that has entered the air inlet, a second filter configured to filter air that has passed the first filter, the second filter having a filter surface including copper, a UV-lamp within an internal space of the housing the UV lamp configured to deliver UV-C light to air that has passed at least the first filter, an air outlet, and an air mover configured to move air between the air inlet and the air outlet, wherein the air purifier is fully powered by a rechargeable power supply and does not require wired connection to wall power, and is configured to sit on a table top.

In still another embodiment of the present disclosure, a wireless air purifier includes a housing having a top and a bottom, an air inlet at or adjacent the top of the housing, a first filter within the housing configured to directly receive air that has entered the air inlet, a second filter configured to filter air that has passed the first filter, the second filter having a filter surface including copper, a UV-lamp within an internal space of the housing the UV lamp configured to deliver UV-C light to air that has passed at least the first filter, an air outlet, and an air mover configured to move air between the air inlet and the air outlet, wherein the air purifier is fully powered by a rechargeable power supply and does not require wired connection to wall power, and is configured to extend from a ceiling.

In yet another embodiment of the present disclosure, an air purifier includes a housing having a top and a bottom, an air inlet at or adjacent the top of the housing, a first filter within the housing configured to directly receive air that has entered the air inlet, a second filter configured to filter air that has passed the first filter, the second filter having a filter surface including copper, a UV-lamp within an internal space of the housing the UV lamp configured to deliver UV-C light to air that has passed at least the first filter, and air outlet, and an air mover configured to move air between the air inlet and the air outlet, wherein the air purifier is configured such that a height of the air inlet is vertically adjustable.

In still another embodiment of the present disclosure, a method for purifying the air of an indoor space includes providing one or more air purifying sites, each one of the one or more air purifying sites configured to filter a sub-volume of the total volume of air in the indoor space, wherein each one of the one or more air purifying sites includes a housing, an air inlet configured to direct treatment air having gaseous and non-gaseous components from the indoor space into the housing, a purifier carried within the housing, an air outlet configured to direct the treatment air that has passed through the purifier into the indoor space, and an air mover configured to move air between the air inlet and the air outlet, through the purifier, operating a first one of the one or more air purifying sites at a first location within the indoor space such that the air inlet is in proximity to the faces of one or more persons, such that exhaled air from the nose and mouth of the one or more persons is pulled into the housing through the air inlet by the air mover, such that it passes through the purifier and exits the air outlet, and operating a central air system to recirculate the total volume of air

BRIEF DESCRIPTION OF THE DRAWINGS

FIG. 5 is an exploded view of the power supply of the air purifier.

FIG. 6 is a partially exploded view of the batter pack of the power supply.

FIG. 7 is a perspective view of the battery pack.

FIG. 9A is a sectional view of an air purifier according to a first alternative embodiment of the present disclosure.

FIG. 9B is a sectional view of an air purifier according to a second alternative embodiment of the present disclosure.

FIG. 15 is a perspective view of a layout of a food or drinking establishment utilizing a plurality of air purifiers, according to an alternative embodiment of the present disclosure.

DETAILED DESCRIPTION OF THE ILLUSTRATED EMBODIMENTS

Figure 1:
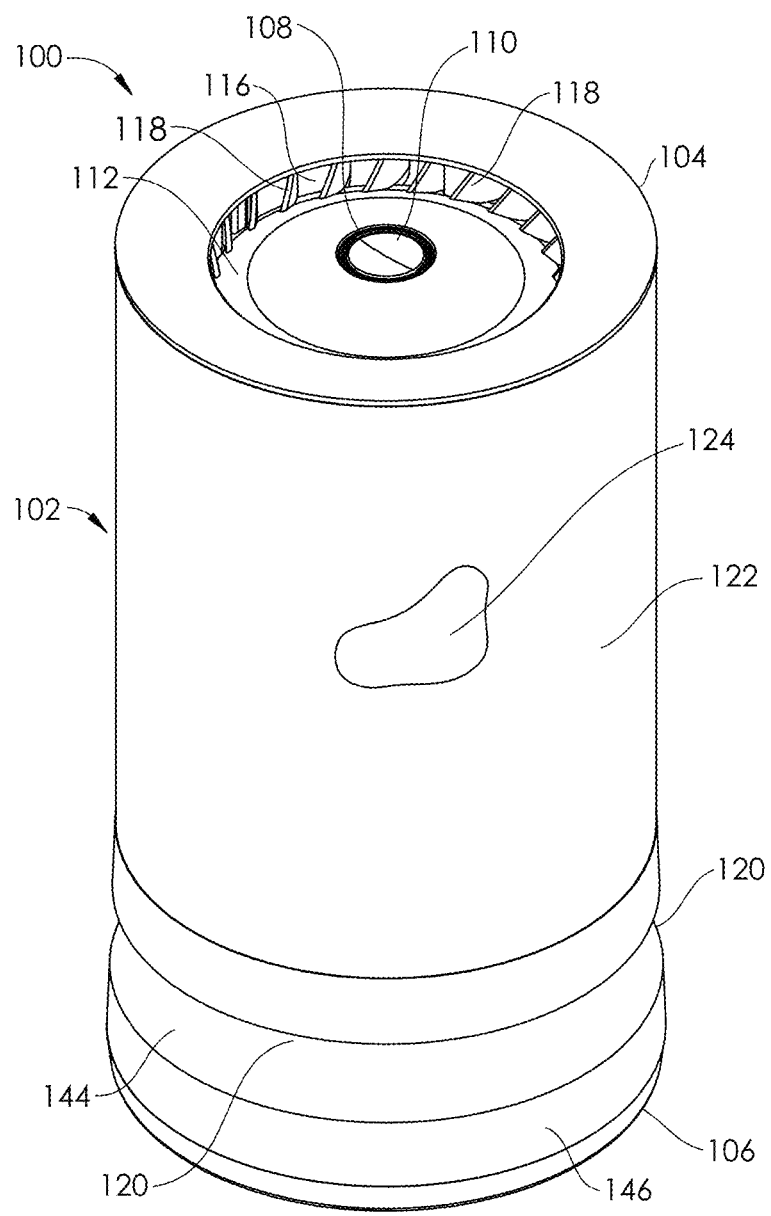
FIG. 1 is perspective view of an air purifier according to an embodiment of the present disclosure.

The present disclosure relates to air purifiers and air purifying systems configured to treat the air within an indoor space for healthful breathing. In many cases, the air within an indoor space may be contaminated primarily by the exhaled air of humans, or other animals within the space. One particular mode of contamination is the spread of virus or bacteria within the exhalant. The SARS-CoV-2 virus that is the basis of COVID-19 is one element that led to the infection of overran estimated 280 million persons on the earth during the global pandemic of the years 2020 and 2021, and that was thought to have been initiated in the year 2019. COVID-19 has been responsible for an estimated 5.4 million deaths, worldwide, reportedly more than 800,000 of which occurred within the United States. Many experts feel that the actual numbers may be greater. Airborne viruses are problematic because they are effectively invisible due to their tiny size, and thus are difficult to detect. In the particular situation related to COVID-19, airborne spread has been shown to be possible, and to be common, in infected persons not yet exhibiting symptoms of the illness. Furthermore, as new variants of COVID-19 have appeared, their contagiousness has been thought to have significantly increased. Businesses, especially restaurants and bars, have struggled to successfully incorporate changing restrictions, that have led to closures, re-openings, re-closures, and more re-openings, each time having to incorporate new regulations and often purchase new equipment or arrangements.

While mask wearing, when consistently practiced, has been effective in slowing the spread of COVID-19, public eating and drinking requires ongoing access to the mouth of the customer. Because the restaurant and bar culture worldwide is usually accompanied by conversation, laughter, and often also accompanied by diminished control due to alcohol intoxication, contaminated exhalant is significantly increased, and results in a much more significant nidus for viral spread. While customers of eating and drinking establishments are understandably concerned about the safety of internal air (air inside the establishment), the reality is that each one of them brings the most significant creator of the risk into the establishment: their exhaled breath. Furthermore, masks only blunt forward motion but do not stop infectious pathogens from entering a building in the air uptake. Masks also have limited value in the build-up of aerosolized virus passing through all the lowest pressure gaps surrounding each mask (path of least resistance).

FIGS. 1-8B illustrate an air purifier 100 configured for treating air within an indoor, outdoor, or semi-indoor or partially indoor space. In one embodiment, the air purifier 100 is configured to be used alone or in conjunction with one or more similar air purifiers 100 to together treat the volume of air within an indoor space. The air purifier 100 is configured to treat a sub-volume of the total volume of air in the indoor space. In some embodiments, a plurality of air purifiers 100 are used together with a central air system within the indoor space. The central air system may in some embodiments comprise an HVAC system that filters and/or treats infected air, and may comprise air recirculation without heat exchange or air recirculation with heat exchange, including heating and/or air conditioning. In other embodiments, the central air system may comprise a fresh air intake system configured to force or allow the entry of outdoor air into the indoor space, and an air exhaust system configured to force or allow the exit of indoor air out of the indoor space. In some embodiments, the indoor space may comprise one or more rooms of a building, and may include a bar, lounge, or restaurant. In some embodiments, the indoor space may comprise any area in which people congregate, including a restaurant, school, symposium or conference or convention, church, an airport waiting area, a line for an attraction at an amusement park, a public building area, a tourist location, a cruise, or a public event. In each case, this may include an indoor space only, an outdoor space only, or a combination of an indoor space and an outdoor space.

Turning to FIG. 1, the air purifier 100 comprises a housing 102 having a first, top end 104 and a second, bottom end 106. Controls 108 for operation of the device include an on/off button 110. When the on/off button 110 is operated to power up the air purifier, air from a local area of a room is pulled within the housing 102 of the air purifier 100 (e.g., by an internal fan 126, FIG. 8A). The air, comprising gaseous and non-gaseous components (e.g. particulates, viruses), enters an inlet or intake area 112 at the top end 104 of the housing 102, and moves into an interior 114 (FIG. 8A) of the housing 102 through one or more passageways 116 that are separated by one or more louvres 118. The air is treated internally and is forced to exit the housing 102 through an outlet area 120, adjacent the bottom end 106 of the housing 102. FIG. 1 illustrates an outer decorative shell 122 that may cover a majority of the outer portion of the air purifier 100. The shell 122 may comprise a particular color, texture, or pattern, and may be designed to match the decorative scheme of the business in which it is used. A logo 124 of the business may also be placed on the shell 122, via painting, printing, engraving, molding, or a decal. In some embodiments, the entire shell 122, including the logo, may be 3D printed.

Figure 2:
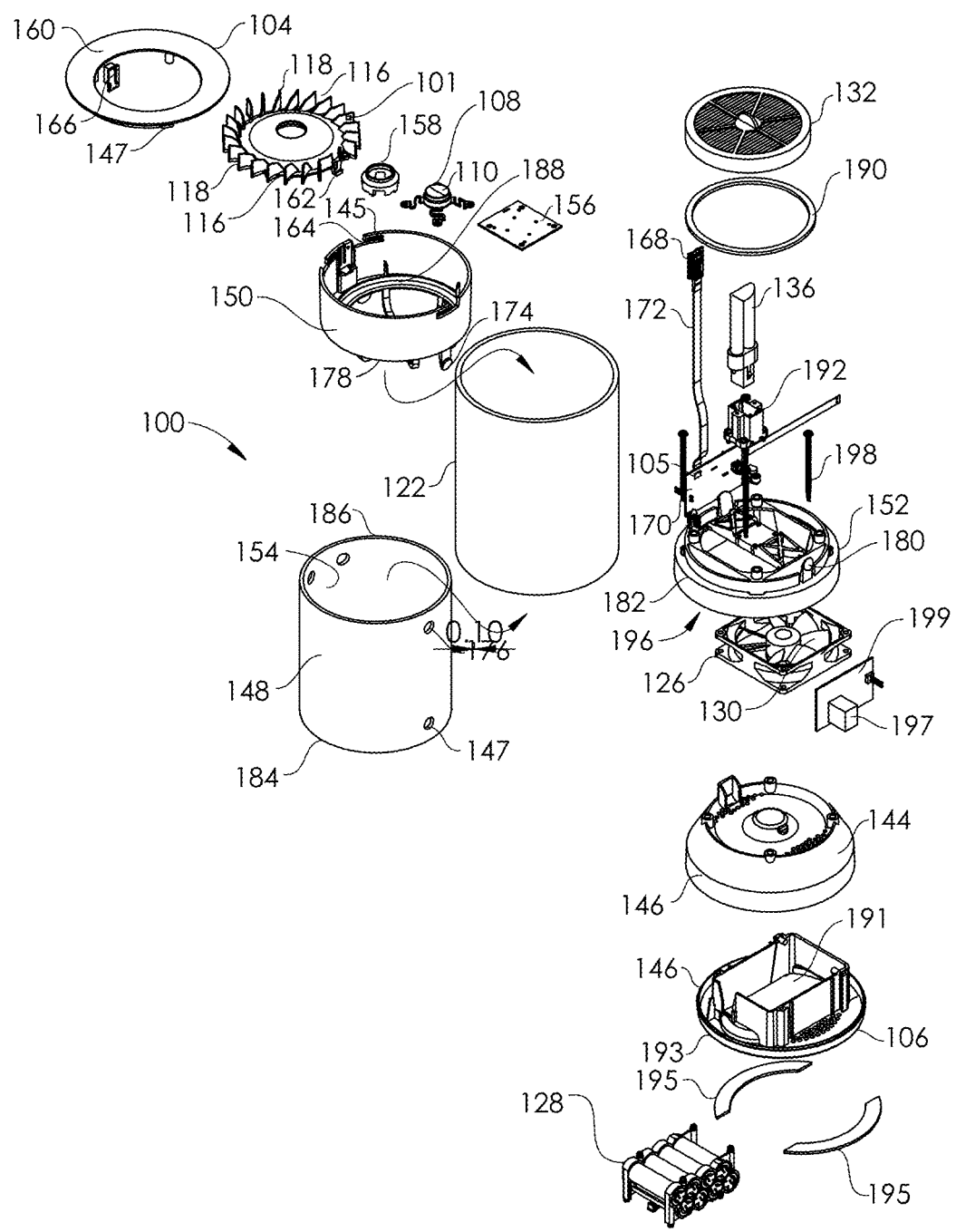
FIG. 2 is an exploded view of the air purifier of FIG. 1.
Figure 8A:
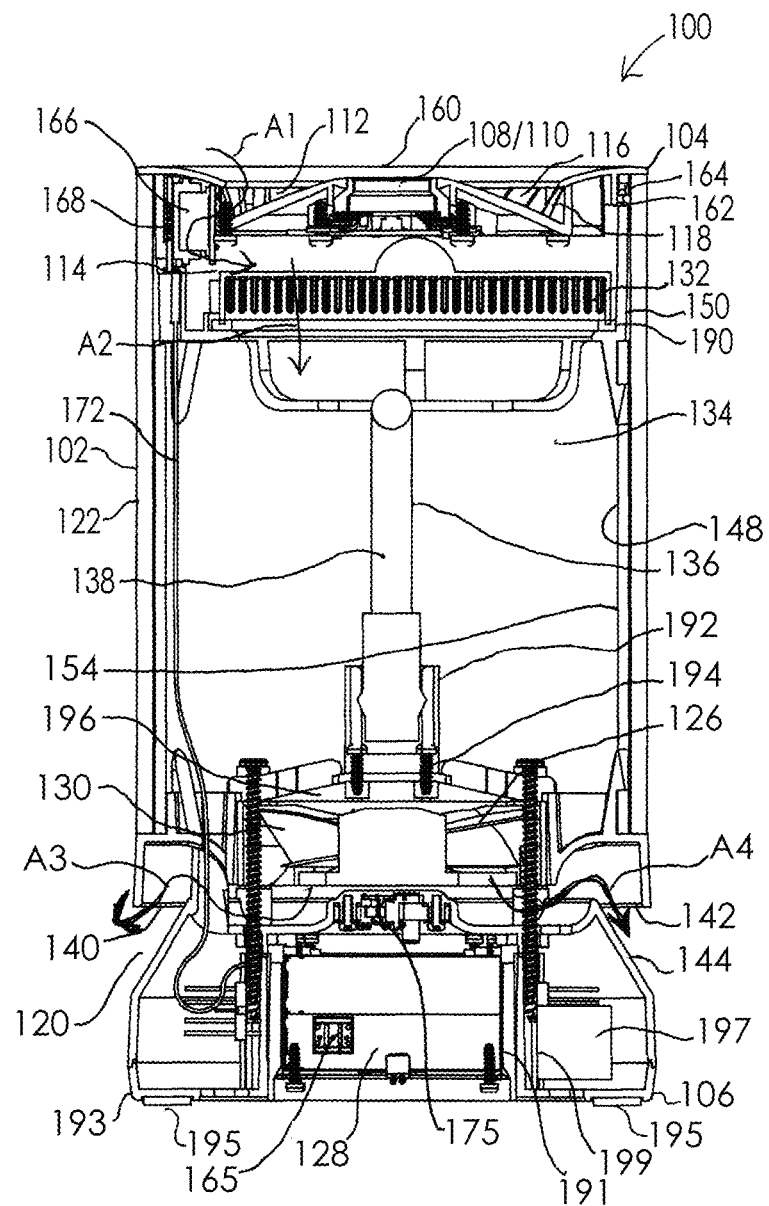
FIG. 8A is a sectional view of the air purifier of FIG. 1.

FIGS. 2 and 8A illustrate internal components of the air purifier 100. Turning first to FIG. 8A, a fan 126 is powered by a removeable, rechargeable power supply 128 and configured such that the fins/blades 130 of the fan 126 rotate in the direction that forces air into the interior 114 via the inlet 112 and passageways 116, causing and air path as shown by arrow A1. Air is then forced through a HEPA filter 132 and into a UV treatment space 134, causing an air path as shown by arrow A2. In some embodiments, the HEPA filter 132 comprises an H10 or higher grade. In other embodiments, the HEPA filter 132 comprises a H13 or higher grade, for example, a medical grade. The HEPA filter 132 may be configured to capture particles 0.10 μm and larger, or configured to capture particles 0.01 μm and larger. The HEPA filter 132 may be configured to capture SARS-COV-2 viruses. The HEPA filter 132 may in some embodiments comprise a Hoover UH 72420 vacuum cleaner-type HEPA filter. The HEPA Filter 132 has a cylindrical shape, but in other embodiments, the air purifier 100 may have a non-cylindrical shape and may utilize a non-cylindrical HEPA filter.

Within the UV treatment space 134, the air that has been filtered by the HEPA filter 132 is exposed to a UV-lamp 136. In recent studies, HEPA filters have been found to be effective in filtering particles under 0.3 μm, and even as small as 0.1 μm, or even smaller. Virus particles can settle on filter surfaces and may be carried in droplets, such as airborne droplets, thus the filter size (e.g., pore size) is not necessarily one-to-one with the size of particles that may be trapped. The SARS-COV-2 virus has been estimated to have a diameter of about 0.125 μm. HEPA filters my filter up to around 99.9% of airborne viruses. Thus, the UV-lamp 136 is configured to disable or kill virus that has passed the HEPA filter 132 without being trapped. The UV-lamp 136 is configured to generate UV-C light within the UV treatment space 134. UV-C light rapidly kills airborne pathogens, and is particularly effective at killing the SARS-COV-2 virus. Thus, the UV-lamp 136 provides germicidal treatment of the pathogens that successfully pass the HEPA filter 132.

The UV-lamp 136 comprises a bulb 138 configured to generate UV-C light, for example UV-C light having a 253.7 nm (254 nm) wavelength. This particular wavelength, like the other wavelengths of UV-C light, does not substantially create ozone $O_3$. Wave lengths above 200 nm do not typically produce ozone, except in transient frequency shifts. In alternative embodiments, the bulb 138 may comprise doped quartz glass to prevent transient frequency shifts that are frequencies in the ozone-producing region. Even a non-ozone-producing frequency can have transient frequency shifts that can produce ozone. Thus, by utilizing the bulb 138 comprising doped quartz glass, the output of treated air from the air purifier 100 does will not significantly contain ozone. The UV-lamp 136 may in some embodiments comprise an OSRAM 23396 5-Watt fluorescent lamp. Thus, catalysts or other mechanisms are not needed to remove ozone, as there is no significant amount of ozone to remove. The fan 126 forces treated air from the UV treatment space 134 out of the housing 102 via tortuous conduits 140, 142, causing air paths as shown by arrows A3, A4. A base 146 (FIG. 1) of the housing 102 includes a substantially conical ramp 144, which serves to distribute the treated air out the outlet 120. The inlet 112 is configured to be at a height of between about six inches and about 14 inches, or between about six inches and about 11 inches, or between about eight inches and about twelve inches, or about ten inches above the bottom end 106 of the housing 102. The inlet 112 is configured to be at a height of fifteen inches or less. Thus, if the air purifier 100 is placed on a table, such as the table of a restaurant, the inlet 112 will be at a height that will be able to efficiently catch a large percentage of the exhalant of persons seated at the table. Persons within sight of the air purifier 100 will be protected from the UV-C light illuminated by the UV-lamp 136 within the housing 102. The louvres 118 are curved and cooperate with each other to keep UV-light from escaping from the housing 102 and thus block the UV-C light from view (to protect eyes) at the top end 104 of the housing 102. Similarly, the tortuous conduits 140, 142 cooperate to keep UV-light from escaping from the housing 102 and thus block the UV-C light from view (to protect eyes) at the bottom end 106 of the housing 102.

Figure 8B:
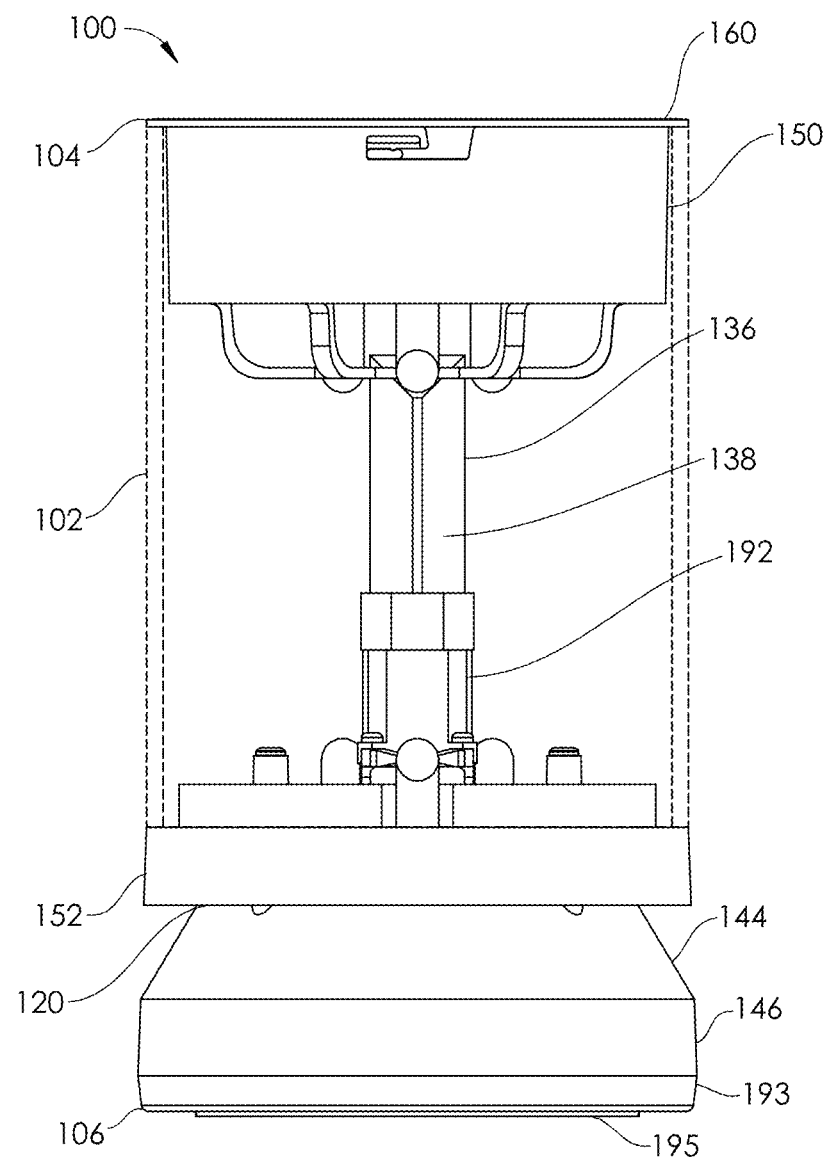
FIG. 8B is detailed view of the UV-lamp of the air purifier of FIG. 1, transverse to the plane of the view of FIG. 8A.

The UV treatment space 134 is defined by an aluminum cylinder 148 held within the shell 122 between a top end piece 150 and a bottom end piece 152 (FIG. 8B, FIG. 2). The aluminum cylinder 148 supports much of the weight of the air purifier 100, and serves and a main structural element. Turning to FIG. 2, tabs 174 extending from a lower portion 178 of the top end piece 150 engage into holes 176 in an upper portion 186 of the aluminum cylinder 148. Tabs 180 extending from an upper portion 182 of the bottom end piece 152 engage into holes 147 at a lower portion 184 of the aluminum cylinder 148. The inner cylindrical surface 154 of the aluminum cylinder 148 is configured to scatter and reflect the UV-C light, and thereby magnify its effective intensity. The aluminum surface 154 when sufficiently polished, may reflect and intensify the light by a multiplication factor of as much as 1.4 (e.g., 133%), or even a multiplication factor of as much as 1.6. The UV-lamp 136 was tested without the aluminum surface 154 to determine dosage at several different distances (from the UV-lamp 136). The UV-lamp 136 was able to provide an average dose of at least about 1.2 mJ/cm$^2$ at a distance of 1.5 inches while the air mover was operating, wherein the residence time of the air within the UV treatment space 134 was about 0.33 second. In some cases, a dose of 1.5 mJ/cm$^2$ was reached at this distance. Thus, with the added effect of the reflective aluminum surface 154, a dose of 1.6 mJ/cm$^2$ to 2.1 mJ/cm$^2$ is achievable. The knowledge of the residence time and the needed dosage allowed the appropriate design input (fan power, UV treatment space size, filter resistance), such that and effective dosage is consistently delivered. The multiplication of the dosage (intensity×time) increases overall efficiency and allows for longer battery (power supply) life.

In other embodiments, the aluminum cylinder 148 may comprise aluminum or another material, and may be coated with a reflective material (e.g., coating) to create a reflective surface capable of reflecting UV light. The reflective coating may be painted, sprayed, dipped, sputtered, or otherwise formed. Overall, the UV-lamp 136 is configured to deliver a dose of at least 1.2 mJ/cm$^2$. In some embodiments, the UV-lamp 136 is configured to deliver an average dose of at least about 2.0 mJ/cm$^2$. The aluminum surface 154 is impervious to the UV-C light, and thus also protects the outside of the housing 102 from the UV-C light. The UV-lamp 136 is able to fill the UV treatment space 134 with UV-C light over the residence time for an "in air kill" of viruses. This is significantly more effective than certain standard germicidal UV-lamps that simply apply UV light (e.g., UV-A, UV-B) to material that is sitting on a surface, for example, on a filter or on an internal wall. The UC-lamp 136 producing UV-C light by applying an average dose of at least about 2.0 mJ/cm$^2$ can inactivate 99.9% of certain aerosolized viruses (e.g., the 0.1% that initially gets past the HEPA filter 132). This is a 3-log reduction. Thus, when the UV-C light is coupled with filtering, at least a 1-log reduction, or at least a 2-log reduction, or at least a 3-log reduction is achievable.

The controls 108 for operation of the device, including the on/off button 110, are carried on a printed circuit board 156, with the on/off button 110 extending from a lightpipe frame 158. A removable ring 160 is rotatably lockable to and rotatably unlockable from the top end piece 150 via elongated tabs 162 that slide into elongated grooves 164 in the top endpiece 150, and protrusions 147 that lock into windows 145 in the top endpiece 150. The ring 160 has a contoured shape that aids in the flow of air into the inlet 112 and the passageways 116. The ring 160 is configured to be removable to allow access to the interior 114 of the housing, including the UV treatment space 134. The ring 160 is turned counter-clockwise to unlock, unsnapping the protrusions 147 from the windows 145, and unsliding the tabs 162 from the grooves 164. An electric plug 166 (or jack) is carried on an outward portion of the removable ring 160. When the ring 160 is in its normal attached position in relation to the top end piece 150, the plug 166 is engaged with a mating plug 168 that couples to a main circuit board 170 via a flex circuit connector 172. The plug 166 and mating plug 168 may in some embodiments be configured to be bayonet-type connectors. The plug 166 must be engaged with the mating plug 168 in order for the UV-lamp 136 to receive power from the main circuit board 170. Thus, when the ring 160 is turned in a counter-clockwise direction, before the tabs 162 completely disengage with the grooves 164, the plug 166 is forced to detach from the mating plug 168, thus removing the ability for the UV-lamp 136 to be powered. It is therefore impossible to open the access to the interior 114 and the UV treatment space 134 with the UV-lamp 136 being lit or lightable, thus ensuring safety and eye protection.

The HEPA filter 132 is sealably held in a flange 188 in the lower portion 178 of the top end piece 150 by an intermediate filter gasket 190. Thus, substantially all of the air entering through the passageways 116 is forced through the HEPA filter 132. The UV-lamp 136 plugs into a socket 192 that is connected via screws 194 to the bottom end piece 152. The socket 192 may in some embodiments comprise a G23 socket. The fan 126 is attached to a cavity 196 on the underside of the bottom end piece 152 with screws 198. A ballast circuit board 199 having a transformer 197 couples the rechargeable power supply 128 to the main circuit board 170 and the power components, including the fan 126 and the UV-lamp 136. These may be coupled to each other via other circuit boards, such as a battery connection circuit board and a power/ballast circuit board. The ballast circuit board 199 provides the appropriate start-up power for the air purifier 100 such that no connection to wall electricity if required. The fan 126 may in some embodiments comprise a Noctua NF-B9 Redux-1600 fan. A lower portion 193 of the base 146 includes a cavity 191 for carrying the power supply 128. Non-abrasive feet 195 are adhesively secured to the lower portion 193 of the base 146, and are may comprise foam, felt, or other compliant materials providing cushioning. The air purifier 100 has an effective footprint of no more than 0.27 foot$^2$, or no more than one foot$^2$. Effective footprint refers to the table space taken by the air purifier 100, whether all of that includes the base where the air purifier 100 sits or not. For example, a lampshade provides the effective footprint of a table lamp, even when the base has a smaller diameter than the lampshade, because the lampshade itself is low enough to block movement and vision. Though a footprint of the air purifier 100 is generally circular, it may also be non-circular. For example, a footprint having a one foot$^2$ footprint may in some cases approximate a rectangle two feet long and six inches wide.

Figure 3:
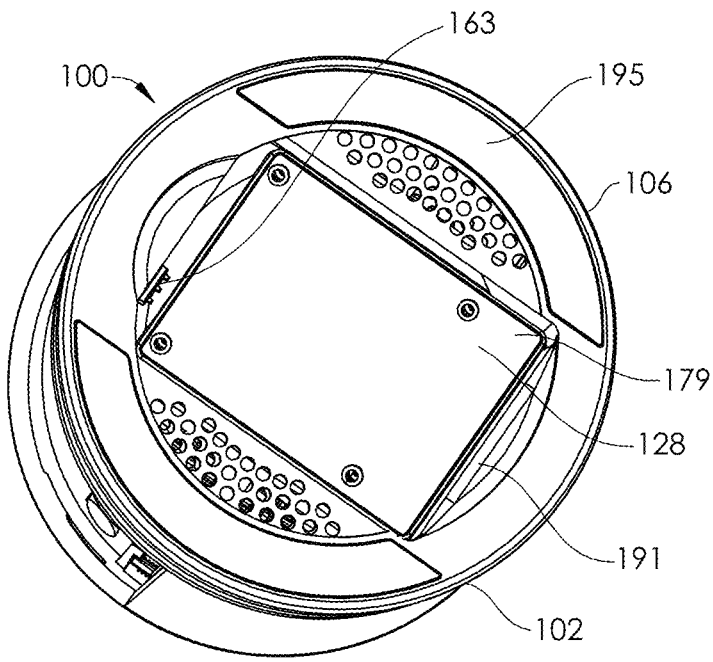
FIG. 3 is a perspective bottom view of the air purifier of FIG. 1.
Figure 4:
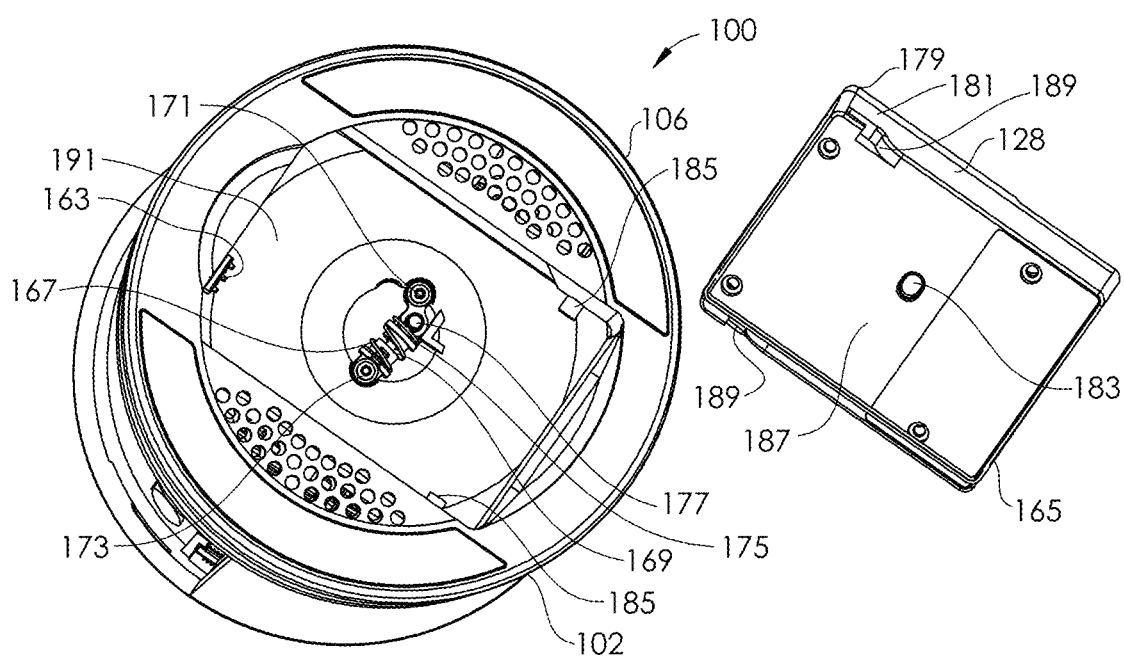
FIG. 4 is a perspective bottom view of the air purifier of FIG. 1 with the power supply removed.

FIGS. 3-7 illustrate the rechargeable power supply 128 having a top casing 179 and a bottom casing 181. The bottom end 106 of the housing 102 is shown in FIGS. 3 and 4, in FIG. 3 with the power supply 128 locked within the cavity 191, and in FIG. 4 with the power supply 128 unlocked and removed from the cavity 191. To engage the power supply 128 into the cavity 191 to power the air purifier 100, curved or tapered grooves 189 on the bottom 187 of the power supply 128 slide over protrusions 185 within the cavity 191. A hole 183 in the bottom casing 181 is configured to be guided by the cavity 191 and the protrusions 185 such that the hole 183 engages a pin 177 of an over-center spring-lock mechanism 175. The over-center spring-lock 175 comprises a first pivot 173, a second pivot 171, a first shaft 169, and a spring 167. When the power supply 128 is slid into place, the pin 177 is forced by the hole 183 to deflect the spring 167, and the curved grooves 189 drop the power supply 128 into place within the cavity 191. The spring-loading of the over-center mechanism 175 locks the power supply 128 within the cavity such that the power supply connector 165 electrically connects to a connector 163 of a connecting PCB or flex circuit, which may contain a safety circuit. Thus, the power supply 128 is removeably connected to the air purifier 100. The power supply 128 is removed by reversing the attachments steps. The quick removal and quick re-attachment after charging by use of the over-center mechanism 175 aids a business such as a restaurant to make quick set-ups and breakdowns at the end of the day and at the beginning of the day, or between shifts, or between mealtimes. The power supply 128 comprises eight batteries 161 electrically connected in two parallel redundant series. The batteries 161 may in some embodiments each comprise an 18650 Lithium-ion cell (18 mm diameter× 65 mm long cylinder cell) having a voltage of 3.7 Volts. The two parallel redundant series of formed of four each of the eight batteries 161 each are capable of supplying 14.8 Volts (at full capacity and charge). Standard operating voltage may be closer to 14.4 Volts. Viewed in series, the parallel connectors comprise a first connector 159, a second connector 157, a third connector 155, a fourth connector 153, and a fifth connector 151. The batteries 161 are held within a frame 149. The first connector 159 and the fifth connector 151 are each configured to electrically join together terminals from two batteries. The second connector, 157, third connector 155, and fourth connector 153 are each configured to electrically join together terminals from four batteries.

As shown in FIG. 2, in some embodiments, a sensor 101 is carried on the air purifier 100 near a passageway 116. In this particular embodiment, the sensor 101 is held on a louvre 118. The sensor 101 may be electrically connected to a circuit board, such as the main circuit board 170, or may be self-powered and wirelessly communicate with the air purifier 100. The sensor 101 is configured to measure a characteristic of air purity. For example, the concentration (e.g., in parts per million) of a particular pollutant, contaminant, or infectant. In some embodiments, the sensor 101 comprises a biosensor. In some embodiments, the sensor 101 comprises a dust or particle sensor. In other embodiments, the sensor 101 may comprise a flow velocity sensor or a pressure sensor, to indicate the effectiveness of the forced air flow of the air purifier 100. The flow velocity or pressure sensor may alternatively be located on an outer portion of the air purifier 100, or even at a location away from the air purifier 100, to indicate the effectiveness of the overall air flow between multiple air purifiers 100 in a particular room or space, or the overall air flow between air purifiers and an internal system (HVAC or air moving system) within the room or space. The data measured by the sensor 101 may be displayed on an external controller (272,372, see FIGS. 12 and 15) or another display, or may be displayed on the controls 108.

Figure 13:
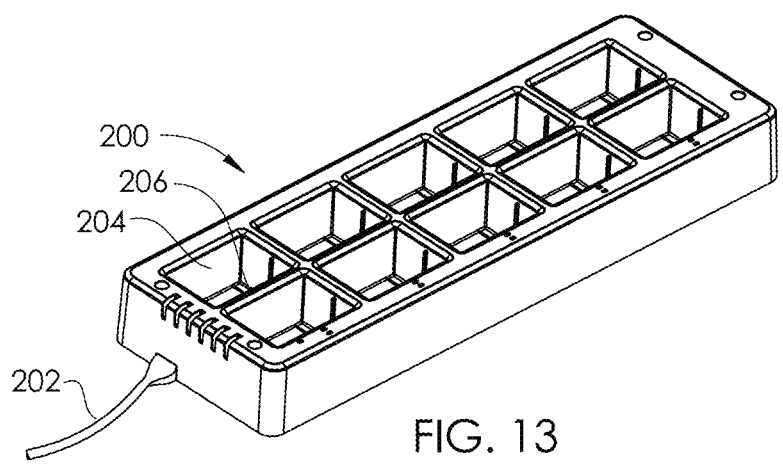
FIG. 13 is a perspective view of a charger, according to an embodiment of the present disclosure.
Figure 14:
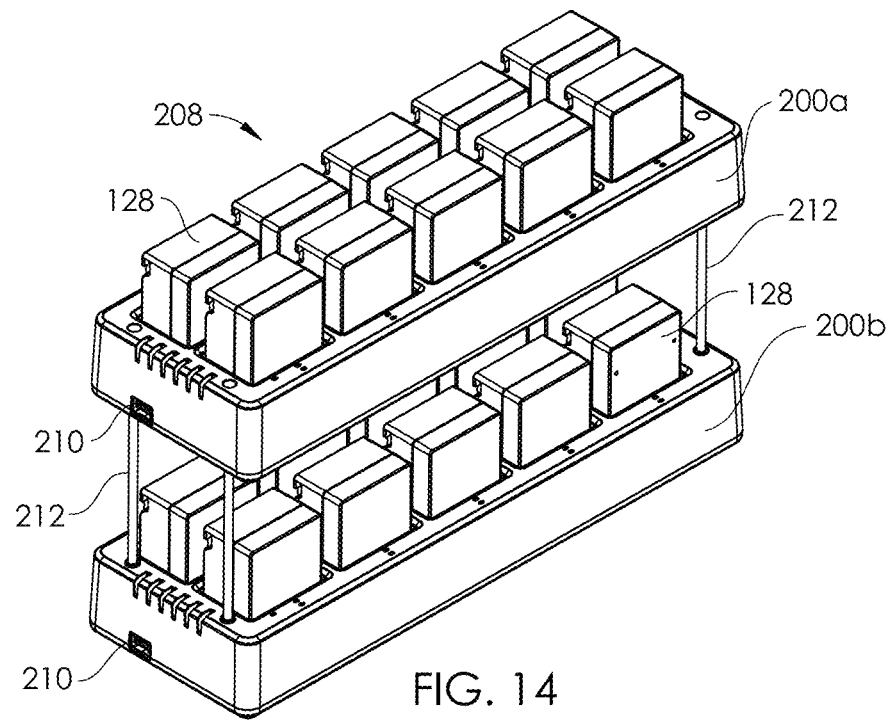
FIG. 14 is a perspective view of two chargers configured for simultaneously charging power supplies of several air purifiers, according to an embodiment of the present disclosure.

Turning to FIG. 13, a charger 200 is configured to charge ten power supplies 128 simultaneously via a single connection (cable 202) to wall power (e.g., 120 Volts-AC, 60 Hz; 240 Volts-AC, 50 Hz; etc.). A restaurant having, for example, eight tables, a bar, and a reception table, may choose to have an air purifier 100 on each of the tables/bar. Because the air purifiers 100 do not have any power cords, the setup is simple, and uncluttered. The restaurant can operate on a schedule of recharging all power supplies 128 at night, when closed, and using all power supplies 128 during the day, including for breakfast, lunch, dinner, and after-dinner. All air purifiers 100 may be kept on their respective table/bar, with the power supplies 128 simply removed and charged each night, and then replaced in the morning in their fully-charged state. The power supply 128, when fully charged, has enough charge capacity to at least continuously power the air purifier 100 for ten hours straight. The power supply 128 may have a capacity of at least 10,000 milliAmpere-hours, or at least 20,000 milliAmpere-hours. The charger 202 comprises ten cavities 204, each having a charging terminal 206 configured to connect to the power supply connector 165 (FIGS. 4-7). FIG. 14 illustrates a charging center 208 of a location utilizing twenty power supplies 128 (e.g., a restaurant with more than ten tables), comprising a first charger 200a and a second charger 200b. The chargers 200a, 200b have not yet been connected to a cable 202 (e.g., cables 202) via their connectors 210. Using two wall outlet plugs (not shown), the twenty power supplies 128 may be simultaneously charged. Risers 212 can be used to tower the chargers 200a, 200b together, so that they do not have an increased footprint.

An alternative air purifier 100a is illustrated in FIG. 9A and includes not only the HEPA filter 132 and the UV-lamp 136, but an additional filter 214. The filter 214 comprises an anti-viral material such as copper. The filter 214 is held within the housing 102 in an additional receptacle 216 between the HEPA filter 132 and the UV-lamp 136, such that the fan 126 moves treatment air through the HEPA filter 132 and the filter 214 (arrow A5) before it enters the UV treatment space 134. The copper filter 214, may comprise a plurality of copper filaments in a matrix, mesh, or weave. Copper provides added filtration, deactivation, and/or destruction of pathogens such as viruses.

An alternative air purifier 100b is illustrated in FIG. 9B and includes not only the HEPA filter 132 and the UV-lamp 136, but an additional filter 218. The filter 218 may also comprise an anti-viral material such as copper, and any of the configurations described in relation to the filter 214. The filter 218 is held within the housing 102 after the HEPA filter 132 and the UV-lamp 136, such that the fan 126 moves treatment air through the HEPA filter 132 and the UV treatment space 134 before it passes the filter 218 (arrow A6). Thus, the UV-lamp 136 is between the HEPA filter 132 and the filter 218. The filters 214, 218 are removable and replaceable, as are the HEPA filter 132 and the UV-lamp 136. The fan 126 is configured to move treatment air out of the air outlet at a rate of at least about 6 cubic feet per minute, or at least about 8 cubic feet per minute, or at least about 10 cubic feet per minute, or at least about 12 cubic feet per minute.

Figure 10:
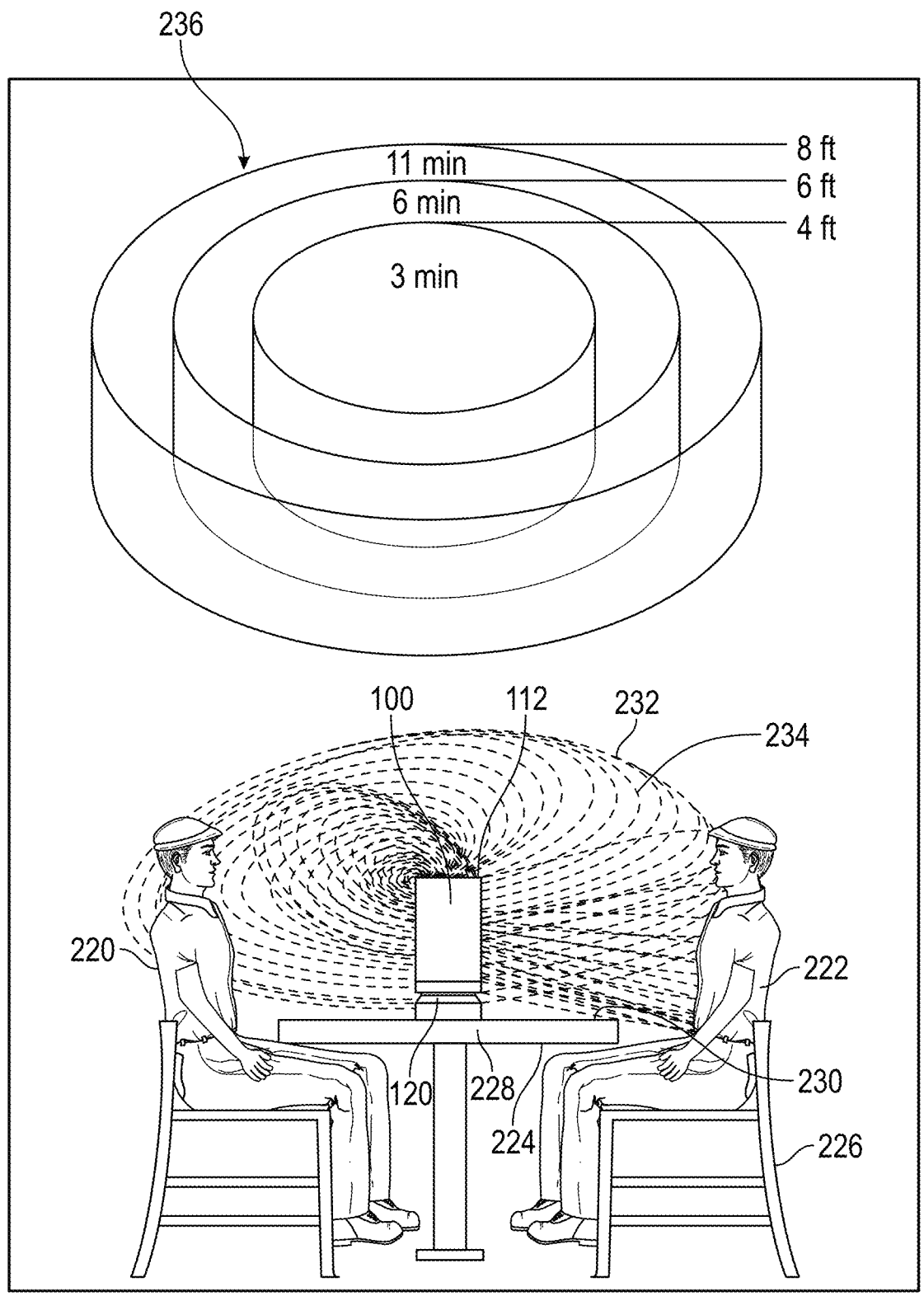
FIG. 10 is a perspective view of the air purifier in use on a table, according to an embodiment of the present disclosure.

FIG. 10 illustrates a first person 220 and second person 222 seated in chairs 226 at a table 224 in a restaurant. An air purifier 100 according to any of the embodiments described herein has been placed in a central location 228 on the top 230 of the table 224. The local air 232 includes a vortex or air pattern 234 that includes currents that bring the exhalant of the persons 220, 222 to the inlet 112, and the currents of the treated air leaving the outlet 120. Thus, the air purifier 100, by itself or in cooperation with other air purifiers 100 in the restaurant, created the vortex 234. A chart 236 at the top of FIG. 10 illustrates the time for air purification through the air purifier 100 of local air 232 at a distance of four feet (three minutes), six feet (six minutes), and eight feet (eleven minutes). These times have been measured in relation to the air purifier 100 of the embodiment described in relation to FIG. 1.

Figure 11:
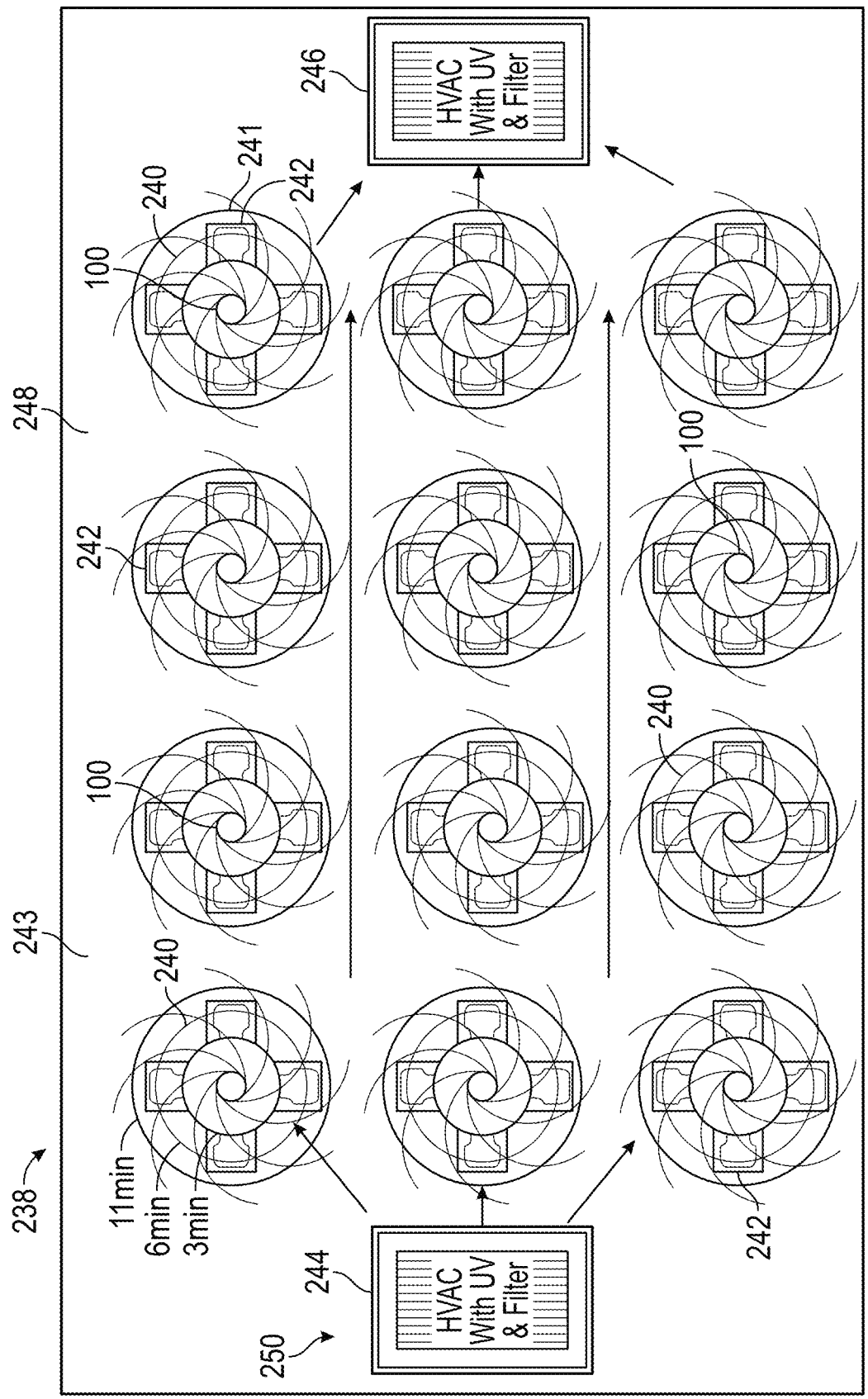
FIG. 11 is an elevational view of a room utilizing a plurality of air purifiers and an HVAC system, according to an embodiment of the present disclosure.

FIG. 11 illustrates a restaurant 238 comprising a dining room 248 having twelve tables 240, arrayed in three rows of four tables 240. Each table 240 includes a table-top air purifier 100 (or air purifying site 100), and four chairs 242. An HVAC system 250 comprising at least one intake 244 and at least one HVAC exhaust 246 are included within the dining room 248. The intake 244 brings air into the dining room 248 and the exhaust removes air from the dining room 248. The HVAC system 250 works cooperatively with the air purifiers 100 to clean and purify the entire space of the dining room 248. A restaurant 238 having multiple rooms such as the room 248 would include a multiple representation of the room 248 of FIG. 11. A plurality of air purifiers 100 in combination with the HVAC system can "turn over" the air in a 600 ft$^2$ room in three to fifteen minutes. It is possible to turn over 8,000 ft$^3$ to 32,500 ft$^3$ of air within fifteen minutes using an HVAC system and 10 to 40 air purifiers 100, or to turn over 16,500 ft$^3$ to 24,000 ft$^3$ of air within fifteen minutes using an HVAC system and 20 to 30 air purifiers 100. Local air 241 is purified by the air purifier 100 at each table. The indoor air 243 is fully purified by the cooperative operation of each air purifier 100 with the HVAC system 250.

Figure 12:
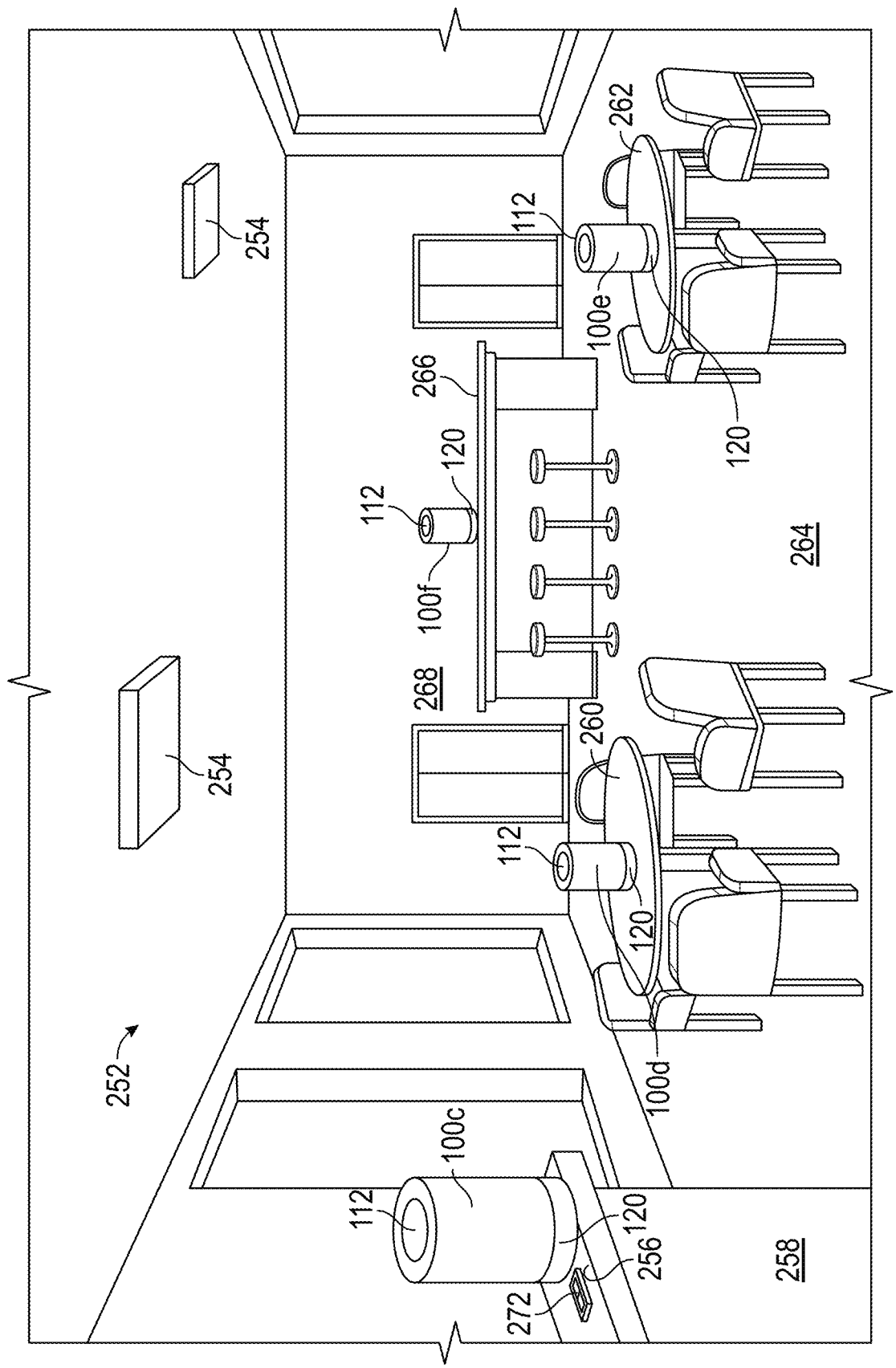
FIG. 12 is a perspective view of a layout of a food or drinking establishment utilizing a plurality of air purifiers, according to an embodiment of the present disclosure.

FIG. 12 illustrates the layout of a restaurant 252 having an HVAC system 254, a reception table 256 within a first room 258, two dining tables 260, 262 within a second room 264, and a bar 266 within a bar area 268. A first air purifier 100c (or air purifying site 100c) sits upon the reception table 256, a second air purifier 100d sits upon a first dining table 260, a third air purifier 100e sits upon a second dining table 262, and a fourth air purifier 100f sits upon the bar 266. The air purifiers 100c-100f are of appropriate heights such that the inlets 112 are relatively in the vicinity of the mouths and nose of the customers in the respective areas. The air purifiers 100c-100f operate together with the HVAC system 254 to recirculate and purify the air of the first room 258, the second room 264, and the bar area 268.

A central controller 272 is shown in the reception table 256, but may be located at any other appropriate area of the restaurant 252. The central controller 272 is configured to wirelessly communicate information back-and-forth to and from the air purifiers 100c-100f, and may be configured to turn one or more of the air purifiers 100c-100f off or on. Each air purifier 100 may include a wireless communication chip 105 (for example, coupled into the main circuit board 170, see FIG. 2), or a transceiver, to allow it to communicate with the central controller 272, and/or to allow it to communicate with each or some of the other air purifiers 100. The central controller 272 may even be configured to receive data from each air purifier 100c-100f whether there are customers in its vicinity, and then turn the air purifier 100c-100f off accordingly. The central controller 272 may receive information from the air purifiers 100c-100f related to: the level of battery charge, the rate of air flow, air pressure, contamination level, the on or off status of air flow, filter usage status, an internal temperature, a temperature at or adjacent the air outlet, and the UV-lamp usage status.

FIG. 15 illustrates the layout of a restaurant 352 having an HVAC system 354, a reception table 356 within a first room 358, two dining tables 360, 362 within a second room 364, and a bar 366 within a bar area 368. A first air purifier 300c (or air purifying site 300c) having an inlet 312 and an outlet 320 is telescopically lowerable and raisable from the ceiling 370 directly above the reception table 356, a second air purifier 300d telescopically extends from the ceiling 370 directly above a first dining table 360, a third air purifier 300e telescopically extends from the ceiling 370 directly above a second dining table 362, and a fourth air purifier 300f telescopically extends from the ceiling 370 generally above the bar 366. A fifth air purifier 300g, also above the bar 366, is shown retracted into the ceiling 370 and is shown not being currently in use. In a busier bar business time, the fifth air purifier 300g can be lowered in operating location. The currently operating air purifiers 300c-300f have been adjusted to appropriate heights such that the inlets 312 are relatively in the vicinity of the mouths and nose of the customers in the respective areas 358, 360, 362, 366. The air purifiers 300c-300f operate together with the HVAC system 354 to recirculate and purify the air of the first room 358, the second room 364, and the bar area 368. The plurality of air purifying sites 300c-300g working cooperatively with the HVAC system 354 are configured to substantially recirculate air from the total volume of the indoor space at a turnover rate of at least about 160 cubic feet per minute, or at least about 240 cubic feet per minute, or at least about 320 cubic feet per minute. Additional air purifiers 100, 300 may be placed for other locations, or other rooms, including bathrooms, kitchen, or entertainment areas. Air purifiers 100 such as those in FIG. 12 and air purifiers 300 such as those of FIG. 15 may be mixed and matched in any particular room or location, depending on the height of the table or bar, the total area of the room or location, the average number of people using the room or location, the average height of the people that use the bar or location, whether the room or location has typically sitting, standing, or reclining people, or moving/mobile people.

A central controller 372 is shown in the reception table 356, but may be located at any other appropriate area of the restaurant 352. The central controller 372 is configured to wirelessly communicate information back-and-forth to and from the air purifiers 300c-300g, and may be configured to turn one or more of the air purifiers 300c-300g off or on. Each air purifier 300c-300g may include a wireless communication chip 105 (for example, coupled into the main circuit board 170, see FIG. 2), or a transceiver, to allow it to communicate with the central controller 372, and/or to allow it to communicate with each or some of the other air purifiers 300c-300g. The central controller 372 may even be configured to receive data from each air purifier 300c-100g whether there are customers in its vicinity, and then turn the air purifier 300c-100g off accordingly. The central controller 372 may receive information from the air purifiers 300c-100g related to: the level of battery charge, the rate of air flow, air pressure, contamination level, the on or off status of air flow, filter usage status, an internal temperature, a temperature at or adjacent the air outlet, and the UV-lamp usage status.

An overall system having a plurality of air purifiers 100, 300 and an HVAC system 254, 354 creates a clean air environment with an overall environment, such that local air is cleaned and the overall air in the defined space is cleaned. Thus, the system works simultaneously on a "micro" and "macro" sense, or in a "component" and "whole" sense. Unlike air purifiers that are designed to simply turn over the entire air of a room over a period of time (e.g., one hour), which may redundantly treat some air while missing other air, the systems described herein are configured to purify the local air of patrons continuously, where the patrons are exhaling and inhaling.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

For purposes of the present disclosure and appended claims, the conjunction "or" is to be construed inclusively (e.g., "an apple or an orange" would be interpreted as "an apple, or an orange, or both"; e.g., "an apple, an orange, or an avocado" would be interpreted as "an apple, or an orange, or an avocado, or any two, or all three"), unless: (i) it is explicitly stated otherwise, e.g., by use of "either . . . or," "only one of," or similar language; or (ii) two or more of the listed alternatives are mutually exclusive within the particular context, in which case "or" would encompass only those combinations involving non-mutually-exclusive alternatives. For purposes of the present disclosure and appended claims, the words "comprising," "including," "having," and variants thereof, wherever they appear, shall be construed as open-ended terminology, with the same meaning as if the phrase "at least" were appended after each instance thereof.

What is claimed is:

1. An air purifying system for a room of an indoor space, comprising:
    a plurality of air purifying sites, each one of the plurality of air purifying sites configured to treat a sub-volume of a total volume of air in the room, wherein each one of the plurality of air purifying sites comprises:
a housing having a top and a bottom;
an air inlet at or adjacent the top of the housing and configured to direct treatment air having gaseous and non-gaseous components from the room into the housing, the air inlet configured for placement in proximity to faces of one or more persons utilizing the room in sitting, standing, or reclining positions;
a purifier carried within the housing;
an air outlet configured to direct the treatment air that has passed through the purifier into the indoor space, the air outlet spaced from the air inlet such that it is configured to be located away from the faces of the one or more persons; and
an air mover configured to move air between the air inlet and the air outlet, through the purifier; and
a controller configured to control operation of the plurality of air purifying sites to treat the total volume of air.

2. The system of claim 1, wherein the purifier comprises a UV lamp configured to deliver UV-C light.

3. The system of claim 1, wherein the purifier comprises a filter comprising copper.

4. The system of claim 1, wherein the housing is configured to be telescopically adjusted.

5. The system of claim 1, wherein the housing is configured to extend upward from a floor of the room.

6. The system of claim 1, wherein the housing is configured to rest on an elevated planar surface.

7. The system of claim 6, wherein the air inlet has a height from the bottom of the housing of between about eight inches and about twelve inches.

8. The system of claim 6, wherein each one of the plurality of air purifying sites has an effective footprint of no more than 0.27 foot$^2$.

9. The system of claim 1, wherein the controller is configured to receive data from the plurality of air purifying sites, the data including one or more characteristics selected from the list consisting of: the level of battery charge, the rate of air flow, air pressure, contamination level, the on/off status of air flow, filter usage status, internal temperature, temperature adjacent an air outlet, and lamp usage status.

10. A method for purifying the air of a room of an indoor space, comprising:
providing two or more air purifying sites, each one of the two or more air purifying sites configured to filter a sub-volume of a total volume of air in the room, wherein each one of the two or more air purifying sites comprises:
a housing having a top and a bottom;
an air inlet at or adjacent the top of the housing configured to direct treatment air having gaseous and non-gaseous components from the room into the housing;
a purifier carried within the housing;
an air outlet on the housing and configured to direct the treatment air that has passed through the purifier into the indoor space, the air outlet spaced from the top of the housing; and
an air mover configured to move air between the air inlet and the air outlet, through the purifier;
operating a first one of the two or more air purifying sites at a first location within the indoor space such that a first air inlet of the first one of the two or more air purifying sites is in proximity to faces of a first one or more persons, such that exhaled air from the first one or more persons is pulled into a first housing of the first one of the two or more air purifying sites through the first air inlet by a first air mover of the first one of the two or more air purifying sites, such that it passes through a first purifier of the first one of the two or more air purifying sites and exits a first air outlet of the first one of the two or more air purifying sites;
operating a second one of the two or more air purifying sites at a second location within the indoor space such that a second air inlet of the second one of the two or more air purifying sites is in proximity to faces of a second one or more persons, such that exhaled air from the second one or more persons is pulled into a second housing of the second one of the two or more air purifying sites through the second air inlet by a second air mover of the second one of the two or more air purifying sites, such that it passes through a second purifier of the second one of the two or more air purifying sites and exits a second air outlet of the second one of the two or more air purifying sites; and
controlling the operation of the two or more air purifying sites with a controller to treat the total volume of air.

11. The method of claim 10, further comprising:
operating a central air system to recirculate the total volume of air.

12. The method of claim 10, further comprising:
controlling the temperature of at least the exhaled air that exits the first air outlet.

13. The method of claim 12, wherein controlling the temperature comprises sensing a first temperature with at least one temperature sensor and changing the first temperature with at least one heat exchanger.

14. The method of claim 10, further comprising:
changing a vertical distance between the first air inlet and a ceiling of the room.

15. The method of claim 10, wherein operating the first one of the two or more air purifying sites further comprises:
delivering UV-C light to at least the exhaled air that passes through the first purifier.

16. The method of claim 15, wherein delivering UV-C light comprises delivering an average dose of at least about 1.2 mJ/cm$^2$.

17. The method of claim 15, wherein delivering UV-C light comprises reflecting the UV-C light with an internal wall.

18. The method of claim 17, wherein the internal wall comprises a reflective coating.

19. The method of claim 10, wherein operating the first one of the two or more air purifying sites further comprises:
causing via the first air mover an outflow rate at the first air outlet of a least about 10 cubic feet per minute.

20. The method of claim 10, wherein operating the first one of the two or more air purifying sites further comprises:
filtering at least the exhaled air with a filter comprising copper.

21. The method of claim 10, wherein each one of the two or more air purifying sites has an effective footprint of no more than one foot$^2$.

22. The method of claim 21, wherein each one of the two or more air purifying sites has an effective footprint of no more than 0.27 foot$^2$.

23. The method of claim 21, wherein the air inlet of each one of the two or more air purifying sites has a height from a bottom of the site of between about eight inches and about twelve inches.

24. The method of claim 10, wherein controlling the operation of the two or more air purifying sites with the controller comprises wirelessly controlling the operation of the two or more air purifying sites with the controller.

25. The method of claim 10, wherein controlling the operation of the two or more air purifying sites with the controller comprises stopping the operation of the first one of the two or more air purifying sites when the first air inlet is not in proximity to the faces of the first one or more persons.

26. The method of claim 10, wherein operating the first one of the two or more air purifying sites further comprises:
  creating a vortex air pattern.

27. The method of claim 10, further comprising:
  receiving information related to contamination level with the controller.

28. The method of claim 10, further comprising:
  receiving one or more data with the controller, selected from the list consisting of: the level of battery charge, the rate of air flow, air pressure, the on/off status of air flow, filter usage status, internal temperature, temperature adjacent an air outlet, and lamp usage status.

\* \* \* \* \*